(12) United States Patent
Graves et al.

(10) Patent No.: US 6,355,401 B1
(45) Date of Patent: Mar. 12, 2002

(54) METHOD FOR PREPARING A HIGH DEFINITION WINDOW IN A CONFORMALLY COATED MEDICAL DEVICE

(75) Inventors: Richard M. Graves, Angleton; Martin C. Herber, Houston, both of TX (US)

(73) Assignee: Intermedics Inc., Angleton, TX (US)

(*) Notice: Subject to any disclaimer, the term of this patent is extended or adjusted under 35 U.S.C. 154(b) by 0 days.

(21) Appl. No.: 09/347,684

(22) Filed: Jul. 2, 1999

Related U.S. Application Data

(62) Division of application No. 08/966,134, filed on Nov. 7, 1997, now Pat. No. 5,925,069.

(51) Int. Cl.⁷ .............................. A61L 31/00; A61N 1/18
(52) U.S. Cl. ................... 430/319; 430/323; 430/945; 219/121.8; 219/121.82; 219/121.7; 219/121.69; 219/121.68
(58) Field of Search ................. 430/319, 323, 430/945; 219/121.68, 121.69, 121.7, 121.8, 121.82

(56) References Cited

U.S. PATENT DOCUMENTS

| | | | |
|---|---|---|---|
| 4,671,848 A | | 6/1987 | Miller et al. ............... 156/643 |
| 5,201,903 A | * | 4/1993 | Corbett, III et al. .......... 439/55 |
| 5,236,551 A | | 8/1993 | Pan ............................. 156/643 |
| 5,480,416 A | | 1/1996 | Garcia et al. ................ 607/36 |
| 5,529,579 A | | 6/1996 | Alt et al. ..................... 607/36 |
| 5,562,715 A | | 10/1996 | Czura et al. ................ 607/36 |
| 5,580,699 A | * | 12/1996 | Layman et al. ............. 430/311 |
| 5,587,200 A | | 12/1996 | Lorenz et al. ............. 427/2.24 |
| 5,607,475 A | * | 3/1997 | Cahalan et al. .............. 623/11 |
| 5,624,449 A | * | 4/1997 | Pham et al. ................ 606/108 |
| 5,782,645 A | * | 7/1998 | Stobie et al. ............... 439/289 |
| 5,925,069 A | * | 7/1999 | Graves et al. ................ 607/36 |
| 5,935,465 A | * | 8/1999 | Cardineau et al. ..... 219/121.69 |

FOREIGN PATENT DOCUMENTS

WO 98/20590 5/1998 ............ H02G/1/12

OTHER PUBLICATIONS

Svelto, O., "Principles of Lasers", Third Ed., Plenum Press, N.Y., N.Y., pp. 320–321, 1989.*

* cited by examiner

Primary Examiner—Martin Angebranndt
(74) Attorney, Agent, or Firm—Schwegman, Lundberg, Woessner & Kluth, P.A.

(57) ABSTRACT

A method is disclosed for rapidly removing electrically insulative coating material from a portion of the titanium housing of an implantable cardiac pulse generator. Pulsed excimer laser radiation ablates an organic coating, such as parylene or a similar polymer, to micromachine a conductive window having sharply defined boundaries or edges. An implantable cardiac pulse generator having an electrically conductive window produced according to the method is also disclosed. The method is suitable for high volume automated production of face or edge window pulse generators, and is also applicable for removal of biomolecular films from other medical articles.

14 Claims, 3 Drawing Sheets

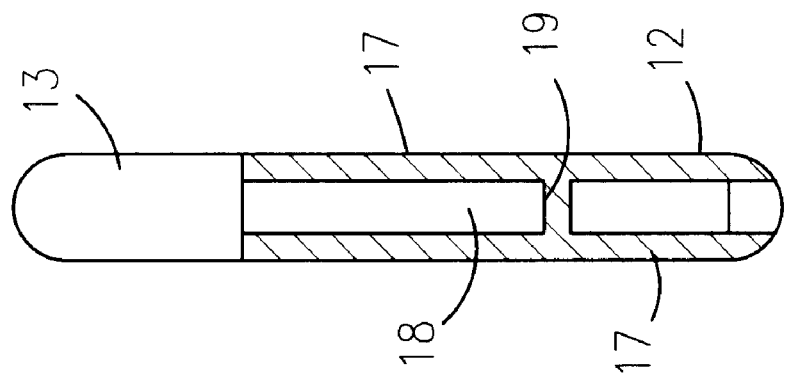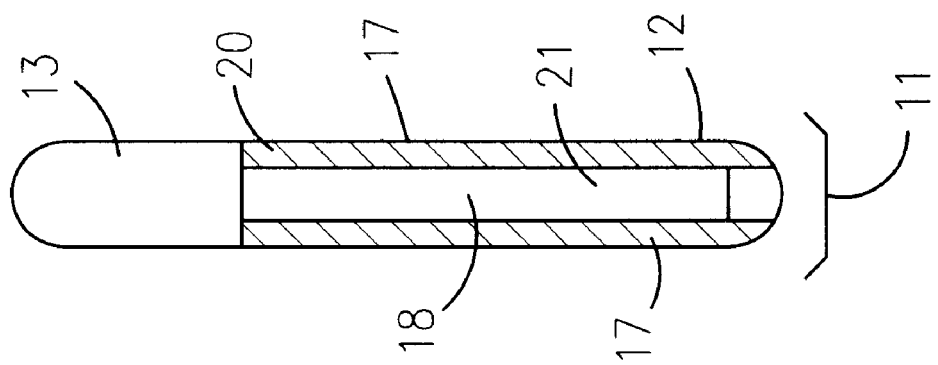

METHOD FOR PREPARING A HIGH DEFINITION WINDOW IN A CONFORMALLY COATED MEDICAL DEVICE

This application is a divisional of U.S. application Ser. No. 08/966,134 filed Nov. 7, 1997 U.S. Pat. No. 5,925,069.

BACKGROUND OF THE INVENTION

1. Field of the Invention

The present invention generally relates to implantable medical devices, particularly cardiac electrical stimulus generators. More particularly, the invention relates to methods of making hot can stimulation electrodes having a conforming electrically insulative biocompatible coating on the housing. The invention relates still more particularly to methods of selectively removing polymeric coating material from such devices to expose a conductive area of the housing.

2. Description of the Related Art

Biocompatible coatings for implantable medical devices are widely employed to avoid adverse body responses to the implanted foreign object. In many modern implantable heart stimulus generators, a biocompatible coating that adheres to and conforms closely about the generator housing (hereinafter "a conformal coating") also serves as an electrically insulative layer covering the generator housing.

In the infancy of implantable cardiac pacemaker therapy, the typical pulse generator case or housing was composed of uncoated metal such as stainless steel, titanium or alloys thereof, and was therefore completely electrically conductive. While this permitted the generator case, or housing, to serve as one of the stimulus electrodes, it also allowed an antenna effect between the generator case and the endocardial electrode tip to occur. When flexation of the pectoral muscle occurred, voltages of similar amplitude and frequency to the intrinsic cardiac signals were produced and conducted through the generator case. Spurious undesirable and potentially dangerous influences on the pacemaker functions resulted, the effects including improper inhibition, and in the dual chamber pacemakers, improper triggering and initialization of reentry tachycardias. In addition to the antenna effects on the pacemaker, each time the pacer emitted an electrical pulse to stimulate the myocardial tissue it also stimulated the patient's pectoral muscle, producing an annoying twitch.

The next generation of pulse generators avoided the muscle-produced improper triggering of the unit by coating the entire electrically conductive case with an electrically insulating material, except for a small uncoated window that allowed the exposed housing surface to serve as the anodal electrode contact. A coating material commonly used for this purpose on pulse generators is typically a thermoplastic polymer film known commercially as parylene, which is both biocompatible and an excellent electrical insulator. In a typical parylene coated unit, the posterior side of the case, meaning all parts facing the (inside) pectoral muscle, all side walls, and part of the anterior (frontal) side of the case are coated with parylene, leaving only a small part of the anterior side of the case to form a forward-facing anodal window that faces the (outside) fatty tissue. This orientation of a "face window" type pulse generator unit greatly reduces muscle-induced interference and has been clinically proven and implemented in many thousands of implantable pacemakers and defibrillators.

Recently, Sulzer Intermedics Inc. provided in U.S. Pat. No. 5,480,416 a cardiac stimulator having its anterior (front) and posterior (back) sides of the case coated with an electrically insulative material such as parylene, but having the edge connecting those two sides at least partially uncoated. Thus, the edge or narrow side of the case functions as the electrically conductive anodal contact surface. This conductive "edge band window" configuration allows for universal implantation orientation of the unit, permitting the pulse generator to be implanted in either the "normal" position conventionally dictated by the placement of the outlets for the connector and lead, or just as conveniently, in the reverse orientation on the opposite side of the body. In this way, the generator case can be turned for left exit or right exit of the electrode lead, and can be implanted in the left or the right side of the patient's chest, at the option of the physician. This edge band window approach also avoids the muscle-induced interference and inappropriate muscle stimulation problems encountered with prior "hot" or "active can" electrodes.

Sulzer Intermedics, Inc. has also developed an implantable defibrillator with the conformal coating partially removed to expose conductive windows (U.S. Pat. No. 5,529,579, issued to Alt et al.).

The window in a conventional parylene coated face window pulse generator is typically formed by an oxygen plasma etch process. The plasma etching process usually employs an aluminum fixture or stencil to define the shape and location of the parylene window on the face of the can. In this process, oxygen is ionized by an RF power supply generated electric field. The ionized oxygen gas cloud, or plasma, reacts with the organic parylene in the window region and forms carbon dioxide gas and water vapor. These gases are subsequently removed by a vacuum. The etch rate is controlled by the RF power and the heat generated at that power. High frequency radio frequency power creates a more reactive plasma than does low frequency power. Higher temperature creates a more reactive plasma, as well. The inherent limitations of the battery inside the pulse generator require that the temperature of the entire unit remain below 60° C. during the etching process, however. This consideration severely limits the rate at which cans can be passed through the window-etching process. Also, it is necessary to maintain electrostatic shielding to prevent undesirable plasma reactions with the vacuum chamber internal surfaces.

Alternatively, the window can be formed simultaneously with the application of the parylene coating, using a masking technique. For the purposes of a human clinical study, for example, Sulzer Intermedics Inc.'s Edge Band units were manufactured by masking the anodal edge region with weld shield tape, parylene coating the entire unit, then removing the tape. This procedure is time consuming, however, and not feasible for large scale production.

U.S. Pat. No. 5,562,715, issued to Czura et al., describes a silicone rubber or parylene coated pacemaker having detachable tabs that are removed at the time of implantation to expose an electrode. One problem with pacemakers employing pull off tabs is that the resulting window in the coating material has jagged or rough edges that leave the remaining coating vulnerable to tearing, peeling or flaking off into the patient's body. A rough-edged parylene coating is especially prone to peeling, tearing or flaking while the unit is being manipulated during surgical implantation and thus allows dislodgment of flecks of the coating into the patient's body. Parylene C is an organic polymer based on p-xylylene,

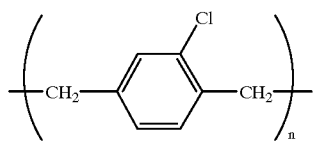

having a molecular weight of about 500,000 daltons. It is used as a thin film coating for such diverse applications as microelectronics, digital display systems, medical devices, dry film lubricants and reflectors for optical devices.[6] Some of the methods that have been used or examined for removing parylene from various surfaces include heating, mechanical/air abrasion, plasma etching, and excimer laser ablation.[1,4]

For cardiac stimulus generators, however, methods that require heating are not suitable because the melt temperature of most polymers is far greater than the maximum 60° C. exposure limit imposed by pacemaker battery manufacturers. Mechanical or air abrasion can create static discharges and make edge and face definition virtually impossible. Plasma etching is too slow, requiring over 10 hours to remove the coating layer from the face of a single pulse generator unit. Because the rate of plasma etching is dependent on temperature, achieving faster results would require exposing the unit to temperatures much higher than the internal components can tolerate. Nevertheless, plasma etching remains the prevailing standard method in the pacemaker industry.

Parylene, and other similar biocompatible coatings, also find widespread application in coating medical devices other than implantable electrical pulse generators. Some of these devices are sensors, probes, transducers, stimulators and prostheses.[7] In many of these devices it may be desirable to provide a window or uncoated portion similar to the pacemaker window described above.

Recently, coatings for medical articles that incorporate functionally active biomolecules capable of eliciting a particular desired effect in the body have been described. For example, U.S. Pat. No. 5,607,475, assigned to Medtronic, Inc., discusses attaching such biofunctional molecules as anticoagulants, thrombolytic agents, cell attachment proteins and anti-inflammatories to coated surfaces of medical devices by way of a covalent bond. It is anticipated that portions of these coatings will likewise need to be removed in some instances.

Hence what is needed is a more efficient way to manufacture high quality implantable medical devices having biocompatible or biofunctional coatings. In particular, a precision method for selectively removing such coatings from certain areas of the device or article is desired.

BRIEF SUMMARY OF THE INVENTION

The present invention provides a rapid and highly effective process for forming a window in a polymeric coating on an implantable medical device such as a cardiac pacemaker or defibrillator. The present process uses an excimer laser to ablate the adherent thin film coating from the underlying UV-resistant surface of the device. The method is particularly applicable to removal of conformal electrically insulative organic polymer film materials, such as parylene, from the metal surface of a "hot can" cardiac electrical stimulus generator. The method of the present invention includes subjecting the coated device to an excimer laser beam for a sufficient time to remove a desired thickness of the coat, or to entirely expose the underlying metal surface inside a window of predetermined size and shape. Preferably the metal surface is UV-resistant, or at least has low susceptibility to erosion by excimer laser. The method also provides for defining a precise configuration of the film to be removed by placing a UV-resistant mask or stencil between the device and the laser beam, in order to make a shaped or patterned window in the coating. A stimulus generator housing prepared by the new method has more sharply defined window edges and a more highly polished exposed metal surface than is typically obtained using conventional plasma etching techniques, and coincidentially provides a more esthetically pleasing appearance than conventional hot cans.

The present invention also provides an improved implantable medical device having a biocompatible organic polymer coating with a window exposing an underlying surface, the improvement including making the opening or window in the coating according to the new method. The edges of the window of the improved device have sharply defined edges that resist peeling or flaking of the coating material from the device. Preferably, the implantable medical device is a "hot can" cardiac stimulation generator and the window serves as an anodal electrode, but it may also be a prosthesis or other implantable medical article having a biocompatible organic coating over a UV-resistant surface and a window or regions of varying thickness in the coating. In some embodiments the biocompatible organic coating is polymeric and comprises a biofunctional molecule.

One embodiment of the invention provides an improved method of making an implantable medical device, or a part of a medical device, that has a window, or ablated area, in an insulative conformal coating that overlies a surface that is substantially resistant to excimer laser erosion. The improved method includes subjecting the device or part to an excimer laser beam for a sufficient time to expose an area of the underlying surface. This new method is especially suitable for use on cardiac pacemakers and defibrillators, particularly those having titanium cases.

Another embodiment of the invention provides a method of removing conformal insulative material from an implantable medical device or part that includes exposing the device or part to an excimer laser beam for a sufficient time to expose an underlying surface that is resistant to erosion by said laser beam. In certain embodiments, the excimer laser susceptible conformal material is electrically insulative, and may contain an organic dielectric in the form of a polymer such as parylene. In some embodiments of the method, a UV resistant mask is interposed between the laser beam and the device or part.

Another embodiment of the invention provides a method of removing an organic coating material from a surface of a medical device or a precursor or component part thereof ("part"). Preferably the surface is resistant to erosion by excimer laser radiation. This embodiment includes providing a source of ultraviolet excimer laser radiation capable of directing a laser beam onto an object at a predetermined point in space; loading the part into a fixture specific to the profile of the part; initiating a computerized controller program; initiating a vacuum hold-down for the part; raising the part pneumatically to a predetermined height fixed by a mechanical stop; initiating a computerized motion program; independently moving X, Y, and rotary axes of said fixture to present an area on the part to a fixed point in space; adjusting the excimer laser source, rep rate, demagnification, number of pulses and etch time, and varying the speed of motion control and distance from the beam to the part, such that a desired level of ablation of the organic coating is achieved; and firing the excimer laser for a sufficient time to permit the irradiated area on the part to receive the desired amount of UV radiation. In certain alternative embodiments, this method is modified to include interposing a UV-resistant mask between the laser radiation source and the part, or moving the part along its X, Y and/or rotary axes while firing the excimer laser.

Still another embodiment of the invention provides an improved implantable medical device, such as a cardiac electrical stimulus generator, or a precursor or component part thereof. In this embodiment, the stimulus generator is of the type having a window in a biocompatible conformal coating, with the window exposing an underlying surface, which may serve as an electrode. Prepared in accordance with the above-described method, the improved stimulus generator has a more highly defined window than that of conventional stimulus generators. This high-definition window may be a "face window" or an "edge band window."

BRIEF DESCRIPTION OF THE SEVERAL VIEWS OF THE DRAWINGS

For a detailed description of a preferred embodiment of the invention, reference will now be made to the accompanying drawings wherein:

FIGS. 2A and 2B are schematic illustrations of alternative embodiments of the edge of a pulse generator case consistent with the present invention.

DETAILED DESCRIPTION OF THE INVENTION

Figure 1B:
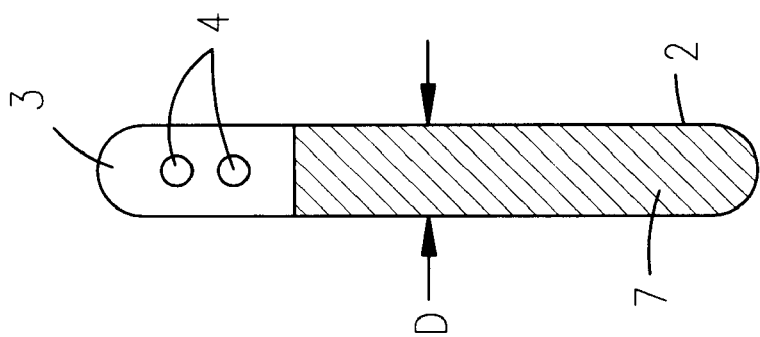
FIGS. 1A, 1B and 1C are schematic illustrations of the front, edge and back, respectively, of certain embodiments of the pulse generator case of the present invention, which in gross appearance is similar to prior art cardiac electrical pulse generator cases prepared using conventional coating methodology.
Figure 1A:
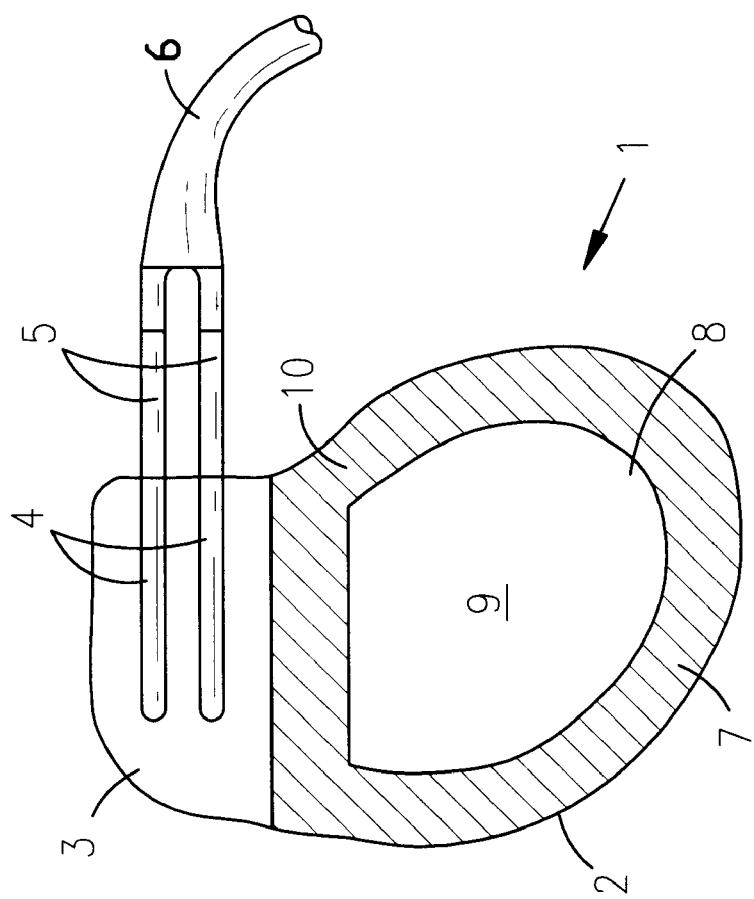
Figure 1C:
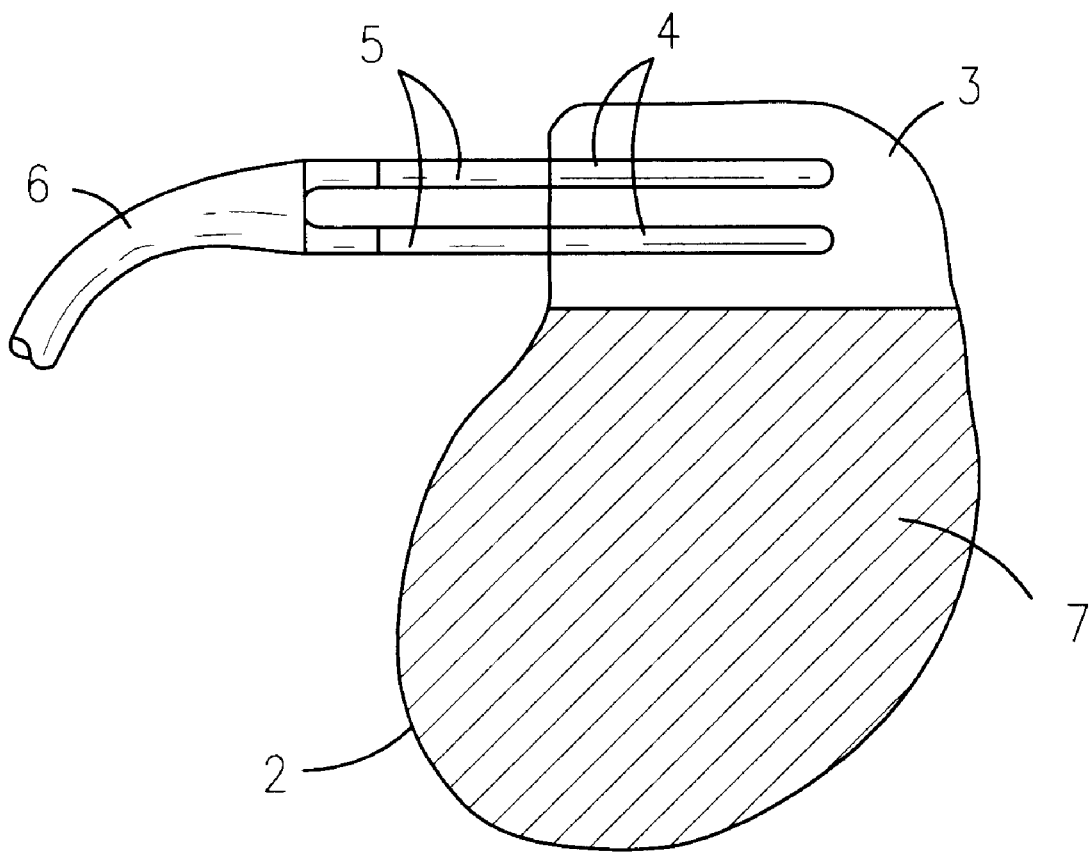

FIGS. 1A–C show the front, side and back of a preferred embodiment of the cardiac stimulus generator 1 of the present invention, which in gross appearance is like a conventional coated hot can stimulus generator. Alternatively, the window may be on the reverse side of the unit (not shown). The housing has a typical coating configuration on the generator case 2. The stimulus generator 1 may be a pacing device of any known type, single or dual chamber, and the case 2 houses the electronics and batteries (not shown) for the generator. In alternative embodiments the stimulus generator may be a "hot can" defibrillator or other device, similar to that described in U.S. Pat. No. 5,529,579 (issued to Alt et al.). The case 2, which in certain embodiments of the invention is oval or slightly pear-shaped, is composed of biocompatible electrically conductive material, such as titanium, and is hermetically sealed against intrusion of body fluids and tissue when implanted into the patient. Atop the case is a header 3, which encapsulates connector receptacles 4 for receiving the connectors 5 of an electrical lead 6. A thin electrically insulative coating or film 7, such as parylene, is indicated in the figures by crosshatching. A window 8 in coating 7 exposes the conductive underlying metal surface 9.

FIG. 2A shows an alternative version of a hot can with a conductive edge band or strip 21 on the narrow side or edge 11 of case 2, and FIG. 2B shows an alternative embodiment having an additional parylene bar 19 interrupting window 18 at desired intervals. The boundaries 20 of window 18 define the exposed metal surface that makes up edge band 21. The exposed metal surface 21 functions as an electrode and its placement on the edge 11 of the case 2 allows stimulus generator 1 to be implanted in either a left or right orientation.

The basic or gross configuration of certain aspects or embodiments of the pulse generator unit of the present invention are essentially as depicted in FIGS. 1A–C and as described in U.S. Pat. No. 5,480,416 (Garcia, et al.), the disclosure of which is incorporated herein by reference to the extent that it provides materials and methods not specifically stated herein. The devices constructed according to the present invention differ from those of the prior art, however, in that because of the way in which window 8, 18 in coating 7 is made, the internal components of the unit are less likely to fail as a result of processing conditions. The window edge 10, 20 and the physical appearance and conductive qualities of the exposed metal surface 9, 21 are better than that of prior art devices. Improvements provided by the present invention are described in more detail below. The coating-removal methods of the present invention are suitable for use with a variety of pulse generator designs and implantable medical devices other than electrical stimulus generators, with only minor modifications. Some of the coated devices for which this excimer laser removal process could be readily adapted include blood pressure sensors, prosthetic components, bone pins, dental implants, probes, ultrasonic transducers, catheters, stents and the like.[8] As mentioned above, today's pacemaker companies rely principally on plasma etching for exposing a non-insulated anodal surface area, such as that shown in FIG. 1A. Plasma etching is extremely slow, resulting in production disadvantages. The method of the present invention utilizes pulsed, intense ultraviolet excimer laser radiation to ablate portions of the insulative coating material to precision machine a conductive window 8, 18 having sharply defined boundaries or edges 10,20. The present technique produces results, including faster processing times, that are far superior to those previously known.

Excimer lasers have been used for various other applications where removal of surface material is desired, including medical procedures such keratotomy, drilling and profiling medical devices such as stents and catheters, and for etching of silicon wafers for the electronic industry[2,3,5]. Pacesetter Inc. has been issued U.S. Pat. No. 5,587,200 for use of an excimer laser to irradiate an atmosphere of titanium, nitrogen, and hydrogen for depositing porous titanium nitride on the surface of an implantable electrode. The present method employing an excimer laser is unique in that it allows the selective removal of conformal insulating material from the surface of implantable pulse generators, or removal of biopolymers or biofunctional molecular coatings from medical devices.

The following examples are offered by way of illustration only and are not intended to limit the scope of the invention in any manner.

Edge Window Ablation

According to a first embodiment, a conductive edge window is formed on a parylene-coated titanium pacemaker using XeCl excimer ablation. The can, which is typically about 6 mm to 8 mm thick, is first coated with a suitable insulating material such as parylene (Union Carbide Corporation, San Diego, Calif. 92123). The insulating material 17 is then removed from an adjoining narrow side or edge 11 so that the resulting edge band window 18 can be used as an electrically conductive anodal contact surface 21, as shown in FIG. 2A. For parylene edge removal, or "edge skiving," the desired part, or unit, is manually loaded into a mechanical fixture specific to the profile of the part. The part may be a complete stimulator unit such as a cardiac pacemaker unit, including a header and a uniformly coated pacemaker housing containing the electronics and power source. A part may also be a defibrillator unit, another medical device or a component thereof. A computerized controller initiates a vacuum hold-down for the part, then raises the pacer pneumatically to a height fixed by a mechanical stop such that the beam is a prescribed distance away from a reference point on the part, such as the epoxy header on a pacemaker. A computerized motion program moves the part along x, y, and rotary axes so as to present the edge 11 of the can 2 to a fixed point in space, with the perimeter moving at a near-constant linear speed. The controller simultaneously fires a XeCl laser so that each portion of the can edge sees the same total dose of laser light. The laser beam is shaped to correspond to the required strip width of the can, using predetermined projection imaging techniques. Suitable laser settings are: rep rate of about 200 Hz, power approximately 40 watts and 20 pulses per beam site at 5:1 demagnification. The excimer laser is preferably operated on the xenon chloride transition at 308 nm with only moderate pulse energy, such as about 250 mJ/pulse for a fluence of about 0.5 J/cm$^2$. At fluences of 15 J/cm$^2$ melting of titanium is known to occur.[9] Alternatively, a krypton fluoride excimer laser at 248 nm can be used.

The laser beam produces a consistent stripping around the elliptical perimeter of the pacer, providing a uniform cosmetic effect. Once the skiving process is completed, the motion system rapidly returns the fixture to the load/unload position, whereupon the next part can be similarly processed. Under the conditions described above, a parylene coating of about 0.00015 to 0.00049 inches initial thickness is removed from the titanium surface in about 30 seconds to form an edge band window. Following excimer laser ablation of parylene from the surface of the can, the exposed titanium is left with an almost mirror surface finish. The rapidity with which laser ablation can be performed permits use of this method for high volume manufacturing of high-definition windowed devices.

In certain alternative embodiments, the part is a defibrillator can and the procedure for preparing the conductive window is essentially the same as described above for a pacemaker case, with minor modification of the fixture to hold the larger, rectangular cans, and minor changes in the focus and the programming of the motion control system to take into account the different contours of the can and the desired window configuration. With only minor alteration of the pacemaker procedure, an adequate strip width and quality is achieved for defibrillator cans.

The excimer laser produces a consistent and well-defined window in the polymer coating around the edge perimeter of the generator case, giving the unit a uniformly smooth, esthetically pleasing appearance. One particular benefit of the excimer laser method is that the parylene coating can be maintained along a radius of curvature of the unit's surface without the splitting or formation of jagged edges that typically occurs with masking and tear-away tabs. As can be seen in FIGS. 1A–C and 2A,B, the coating material should be well adhered to the contours of edge 12, wrap around the corners on the narrow side 11 of the unit and curve along the boundaries of window 8, 18. With conventional techniques, both the masking material and the pull off tabs associated with the coating, by contrast, will tend to loosen and rip the coating material in these regions. It is very difficult to make a fixture that will rest tightly enough on a radius so as to prevent the plasma from penetrating. Still another advantage of the present method is that since the excimer laser treatment does not cause appreciable heating of the substrate surface, the chance of damage to the internal components of the unit due to temperature elevation during processing is negligible. In addition, even if the processing apparatus were to jam, such that the substrate was exposed to the laser beam for an extended period, there would be no damage to the internal components as the preferred laser wave length causes no appreciable heating of the titanium. Another advantage is that, with a cycle time of about 25–30 seconds per unit, the present excimer laser technique lends itself to high volume automated processing applications. If less than total removal of the coating is desired on a particular device or article, the depth of etching of the coating material can be readily managed by controlling the number of pulses, fluence and the motion control system. Other biocompatible organic polymers, such as rubber, are also suitable for use as the electrically insulative coating material. Polymers that are transparent to UV radiation, but are otherwise suitable as coating material, can be doped with a biocompatible UV absorbing compound to increase susceptability of the polymer to excimer laser ablation. Electrically conductive housing materials other than titanium, such as stainless steel, platinum or titanium alloys can likewise be substituted, provided that the material resists high energy ultraviolet laser radiation, or is much less susceptible to excimer laser than the coating layer being removed.

For stimulus generators coated with parylene, the electrically insulating material is ablated by the laser with virtually no heating of the underlying structures, as the energy is absorbed in the first 0.1 to 0.5 microns of material. Parylene is transparent to conventional visible laser frequencies, however, it is opaque to UV radiation. The ablated material is removed layer by layer on a pulse-by-pulse basis. Because of the submicron depth of penetration of each pulse, very fine control of the depth of cutting is obtained. Also, the majority of the energy in the laser pulse is used in bond breaking and in ejecting ablated material from the substrate. Consequently, very little energy remains in the substrate and thermal diffusion to surrounding areas is negligible.

Coating ablation by excimer laser processing provides the advantage of removing material with extremely high precision and excellent edge definition. There is no significant charring or burning of surrounding material and any heat-affected zone is minimal. Use of the excimer laser method described herein permits selective removal of material from an underlying substrate that leaves the substrate virtually unaffected. The excimer laser technique also permits definition of patterns by mask imaging rather than by translation of a focused spot, for certain applications.

Face Window Ablation

According to an alternative embodiment, a conductive face window is formed in a parylene coated titanium pacemaker case by XeCl excimer ablation by modification of the method described above for edge window ablation. For removal of parylene from the can face ("face skiving") rather than the edge, the part is manually loaded into a fixture specific to the profile of the part, as described above. The fixture includes a contact mask that defines the area where parylene is to be removed. The contact mask is itself made of metal or another excimer laser resistant material, and may be attached to the fixture as a flip-up lid with a contact mask attached. Preferably, the maximum contact force for the can against the mask is about 10 pounds. Optics form the beam into a thin line long enough to cross the shortest dimension of the mask opening. A computer program again initiates vacuum hold-down, raises the pneumatic cylinder, and positions the unit under the beam, and fires the excimer laser, using multiple pulses, to achieve uniform removal of the coating. The unit is translated under the beam at a uniform rate using essentially the same conditions and demagnification described for the edge band removal, because the parylene coating thickness is uniform. Using multiple pulses to achieve uniform removal of the coating, about two passes of the unit under the beam are sufficient. The cycle time for face ablation of parylene is about 50 seconds per unit. The definition of the resulting window is more obvious and is esthetically more pleasing due to its shiny appearance than is obtainable using plasma etching techniques.

According to a third embodiment of the present invention, an alternative biomolecular film is ablated from a medical device. Recently, coatings have been developed for body-contacting medical devices that incorporate functionally active biomolecules capable of eliciting a particular desired effect in the body. U.S. Pat. No. 5,607,475 discusses biofunctional molecules such as anticoagulants, thrombolytic agents, cell attachment proteins and anti-inflammatories as being suitable for covalently linking to coated surfaces of medical articles. As manufacturers begin to apply coatings of parylene or specific biofunctional materials to the surfaces of various medical devices, selective removal of some of the material will often be necessary. Using essentially the same methods as described above for edge and face window ablation, with only minor modifications to take into account the shape of the part and the excimer laser susceptibility of the particular biomaterial, excimer laser radiation is applied to a coated article to selectively remove the desired amount of the coating. This excimer laser method will also be of great value in manufacturing new medically related articles, such as those coated with the new biofunctional materials.

While certain embodiments of this invention have been shown and described in the foregoing examples, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims which follow, the scope of which shall include all equivalents of the subject matter of the claims.

REFERENCES

1. Znotins, Thomas A., Darcy Poulin and John Reid, "Excimer Lasers: An Emerging Technology in Materials Processing," *Laser Focus/Electro-Optics,* May 1987, pp. 54–70.
2. Srinivasan, R., "UV Laser Ablation of Polymers and Biological Tissues," *Lambda Highlights,* No. 1, published by Lambda Physik, October 1986, 2 pgs.
3. Schaeffer, Ronald, "Laser Micromachining of Medical Devices," *Medical Plastics and Biomaterials,* May/June 1996, pp. 32–38.
4. "Excimer Laser Removal," in "Repair and Recoating of Parylene Coated Printed Circuit Boards," August 1994, published by Specialty Coating Systems, Indianapolis, Ind., p. 10.
5. Schaeffer, Ronald D., "Laser-Manufactured Features in Medical Catheters and Angioplasty Devices," *Medical Device & Diagnostic Industry,* November 1996, pp. 61–64.
6. "Parylene Conformal Coatings," brochure NTC 7906 of Nova Tran Corporation, Clear Lake, Wis. 54005, 6 pages.
7. "Xylylene Polymers," Specialty Coating Systems, Inc., Indianapolis, Ind. 46241, (August 1994), pgs. 1020, 1021, 1023–1025.
8. "Literature Review: Biological Safety of Parylene C," *Medical Plastics and Biomaterials* (March/April 1996), pgs. 30–35.
9. Tosto, S., A. Di Bartolomeo and P. Di Lazzaro, "Surface Ablation by Excimer Laser Irradiation of Ti and Ti6A14V Alloy," *Appl. Phys.* A63, 385–389 (1996).

What is claimed is:

1. A method of making an implantable medical device, or part thereof, having a high definition face window in an insulative conformal coating comprising subjecting a portion of said device or part having an insulative conformal coating to an excimer laser beam for a sufficient time to expose an underlying surface of said device or part, said surface being resistant to erosion by said laser beam, wherein said coating comprises a biomolecular polymer.

2. The method of claim 1 wherein said device is a cardiac pacemaker.

3. The method of claim 1 wherein said device is a cardiac defibrillator.

4. The method of claim 1 wherein said underlying surface is titanium.

5. The method of claim 1 wherein said conformal material is electrically insulative.

6. The method of claim 1 wherein said electrically insulative material is an organic dielectric.

7. The method of claim 1 further comprising introducing a UV resistant mask between said laser beam and said device or part.

8. A method of making a high definition face window in an organic coating material on a surface of a medical device or a precursor or component part thereof, said medical device, precursor or component part hereinafter referred to as a part, the method comprising:

providing a source of ultraviolet excimer laser radiation capable of directing a laser beam onto an object at a predetermined point in space;

loading the part into a fixture specific to the profile of the part;

initiating a control program;

raising the part to a predetermined height;

initiating a motion program;

independently moving X, Y, and rotary axes of said fixture to present an area on the part to a fixed point in space;

interposing a UV-resistant mask between said laser radiation source and said part;

adjusting the excimer laser source such that a desired level of ablation of the organic coating is achieved; and firing the excimer laser for a sufficient time to permit the irradiated area on the part to receive a desired amount of UV radiation to produce a high definition face window in the coating exposing the underlying UV resistant surface.

9. The method of claim 8 wherein said surface is resistant to erosion by said laser beam.

10. The method of claim 8 further comprising independently moving the part along its X, Y and/or rotary axes while firing the excimer laser.

11. The method of claim 8 wherein the organic coating material is electrically insulative.

12. The method of claim 8 wherein the organic coating material is an organic dielectric.

13. The method of claim 8 wherein the organic coating material is polymeric.

14. The method of claim 8 wherein the organic coating material is parylene.

* * * * *